US00PP26746P2

(12) United States Plant Patent
Hooijman

(10) Patent No.: US PP26,746 P2
(45) Date of Patent: May 24, 2016

(54) ROSE PLANT NAMED 'ESM R136'

(50) Latin Name: *Rosa hybrida*
Varietal Denomination: ESM R136

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 131 days.

(21) Appl. No.: 14/120,579

(22) Filed: Jun. 6, 2014

(51) Int. Cl.
*A01H 5/02* (2006.01)

(52) U.S. Cl.
USPC ..... Plt./108

(58) Field of Classification Search
USPC ..... Plt./108
See application file for complete search history.

*Primary Examiner* — Keith Robinson
(74) *Attorney, Agent, or Firm* — C. A. Whealy

(57) ABSTRACT

A new and distinct cultivar of Rose plant named 'ESM R136', characterized by its upright and strong flowering stems; moderately vigorous growth habit and high productivity; freely flowering habit; bright red-colored flowers that are typically grown as spray types; excellent postproduction longevity; and tolerance to *Botrytis*.

1 Drawing Sheet

Botanical designation: *Rosa hybrida.*
Cultivar denomination: 'ESM R136'.

BACKGROUND OF THE INVENTION

The present Invention relates to a new and distinct cultivar of Rose plant, botanically known as *Rosa hybrida,* commercially used as a cut flower Rose plant, and hereinafter referred to by the name 'ESM R136'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in November, 2008 of a proprietary Rose selection identified as Line 199, not patented, as the female, or seed, parent with a proprietary Rose selection identified as Line 222, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in September, 2009.

Asexual reproduction of the new Rose plant by bud grafting in El Quinche, Pichincha, Ecuador since March, 2010 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R136'. These characteristics in combination distinguish 'ESM R136' as a new and distinct Rose plant:

1. Upright and strong flowering stems.
2. Moderately vigorous growth habit and high productivity.
3. Freely flowering habit.
4. Bright red-colored flowers that are typically grown as spray types.
5. Excellent postproduction longevity.
6. Tolerance to *Botrytis.*

Plants of the new Rose differ from plants of the female parent selection in the following characteristics:

1. Plants of the new Rose are taller than plants of female parent selection.
2. Stems of plants of the new Rose have fewer thorns than stems of plants of the female parent selection.
3. Flowers of plants of the new Rose have fewer petals than flowers of plants of the female parent selection.
4. Plants of the new Rose and the female parent selection differ in flower color as plants of the female parent selection have velvety red-colored flowers.

Plants of the new Rose differ from plants of the male parent selection in the following characteristics:

1. Plants of the new Rose are shorter than plants of the male parent selection.
2. Stems of plants of the new Rose had more thorns than stems of the male parent selection.
3. Flower buds and flowers of plants of the new Rose are slightly larger than flower buds and flowers of plants of the male parent selection.
4. Flowers of plants of the new Rose have fewer petals than flowers of plants of the male parent selection.
5. Plants of the new Rose and the male parent selection differ in flower color as plants of the male parent selection have orange-colored flowers.

Plants of the new Rose can be compared to plants of Rose 'Esm Fant', disclosed in U.S. Plant Pat. No. 18,896. In side-by-side comparisons conducted in El Quinche, Pichincha, Ecuador, plants of the new Rose differed from plants of 'Esm Fant' in the following characteristics:

1. Plants of the new Rose were more freely branching than plants of 'Esm Fant'.
2. Plants of the new Rose had longer internodes than plants of 'Esm Fant'.
3. Stems of plants of the new Rose had fewer thorns than stems of plants of 'Esm Fant'.
4. Inflorescences of plants of the new Rose had more flowers than inflorescences of plants of 'Esm Fant'.
5. Flowers of plants of the new Rose had fewer petals than flowers of plants of 'Esm Fant'.
6. Plants of the new Rose and 'Esm Fant' differed slightly in flower color.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photographs on the left side of the sheet comprise side perspective views of typical flowering stems of 'ESM R136'.

The photograph at the upper right of the sheet is a close-up view of a typical flower of 'ESM R136'.

The photograph at the lower right of the sheet are close-up views of the upper and lower surfaces of typical leaves of 'ESM R136'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were 2.5 years old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R136'.

Parentage:

*Female, or seed, parent*.—Proprietary seedling selection of *Rosa hybrida* identified Line 199, not patented.

*Male, or pollen, parent*.—Proprietary seedling selection of *Rosa hybrida* identified Line 222, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Fibrous, fine to medium in thickness; close to N199B in color.

*Rooting habit*.—Moderately freely branching; medium density.

Plant description:

*Plant and growth habit*.—Perennial shrub; upright and strong flowering stems; typically grown as a spray-type cut flower; moderately vigorous growth habit.

*Branching habit*.—Freely basal branching habit; highly productive with about 7.2 flowering stems developing per plant per year.

*Plant height*.—About 127 cm.

*Plant width (spread)*.—About 55 cm.

*Lateral branches*.—Quantity: About 17 lateral branches develop per plant. Length: About 81 cm. Diameter: About 7 mm. Internode length: About 4.1 cm. Texture: Smooth, glabrous; older stems, woody. Color: Close to N199B and 146A. Thorns: Density: Medium. Shape: Triangular with sharp acuminate apices; slightly incurved and flat. Height: About 9 mm. Length, at base: About 9 mm. Color, immature: Close to 178B and N199D. Color, mature: Close to N199D and 172A.

Leaf description:

*Arrangement*.—Alternate; compound with typically seven leaflets per leaf.

*Leaf length*.—About 17.4 cm.

*Leaf width*.—About 10.2 cm.

*Terminal leaflet length*.—About 5.6 cm.

*Terminal leaflet width*.—About 3.4 cm.

*Lateral leaflet length*.—About 5 cm.

*Lateral leaflet width*.—About 2.9 cm.

*Leaflet shape*.—Ovate.

*Leaflet apex*.—Acute.

*Leaflet base*.—Attenuate.

*Leaflet margin*.—Serrate.

*Leaflet texture, upper and lower surfaces*.—Smooth, glabrous; papery to coriaceous.

*Leaflet venation pattern*.—Pinnate.

*Leaflet color*.—Developing leaflets, upper surface: Close to 139A. Developing leaflets, lower surface: Close to 147B. Fully expanded leaflets, upper surface: Close to 139A; venation, close to 152B. Fully expanded leaflets, lower surface: Close to 147A; venation, close to 146C.

*Petioles, leaves*.—Length: About 2.3 cm. Diameter: About 2 mm. Texture, upper surface: Prickly. Texture, lower surface: Smooth, glabrous. Color, upper surface: Close to 146A and 166A. Color, lower surface: Close to 146C.

*Petioles, leaflets*.—Length: About 2.3 cm. Diameter: About 1.1 mm. Texture, upper surface: Prickly. Texture, lower surface: Smooth, glabrous. Color, upper surface: Close to 146A. Color, lower surface: Close to 144A.

*Stipules*.—Arrangement and appearance: Two, adnate to the petiole, leafy in appearance. Length: About 2 cm. Width: About 1.7 mm. Shape: Roughly deltoid. Apex: Acuminate, tapered. Base: Tapered. Margin: Serrate. Texture, upper and lower surfaces: Irregularly pubescent; membranous. Venation pattern: Pinnate. Color, upper surface: Close to between 139A and 147A. Color, lower surface: Close to 146A.

Flower description:

*Flower type and arrangement*.—Symmetrical rosette flowers; flowers typically grown as spray types; flowers face mostly upright.

*Flowering season*.—Plants of the new Rose flower year-round under greenhouse conditions; early flowering habit, plants begin flowering about 85 days after pinching; in the garden, optimal flowering from spring through autumn; flowering intermittent.

*Spray height*.—About 24 cm.

*Spray diameter*.—About 22 cm.

*Flowering habit*.—Freely flowering habit, about seven to nine open flowers per spray.

*Flower diameter*.—About 6.7 cm.

*Flower depth* (*height*).—About 3 cm.

*Flower longevity on plant*.—Excellent postproduction longevity, flowers maintain good substance for about 28 to 30 days; flowers persistent.

*Flower longevity as a cut flower*.—Excellent postproduction longevity, flowers last about eleven days; flowers persistent.

*Fragrance*.—None detected.

*Flower buds*.—Shape: Ovoid. Length: About 2.9 cm. Diameter: About 1.9 cm. Color: Close to 144A and 175B.

*Petals*.—Quantity: About 26 to 28 per flower; petals imbricate. Length: About 3.1 cm. Width: About 3.5 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Close to 53A; towards the base, close to 1C. When opening, lower surface: Close to 58A; towards the base, close to 160C. Fully opened, upper surface: Close to 53A; towards the base, close to 5C. Fully opened, lower surface: Close to 63A; towards the base, close to 1D.

*Petaloids*.—Quantity: About five; petaloids whorled. Length: Variable. Width: Variable. Shape: Irregularly shaped. Apex: Blunt to shortly acute. Base: Obtuse. Margin: Mostly uneven. Texture, upper and lower surfaces: Smooth, glabrous; papery to coriaceous. Color: When opening and fully opened, upper surface: Close to 53A; towards the base, close to 6C and 4D. When opening and fully opened, lower surface: Close to 53A; towards the base, close to 5A and 150D.

*Sepals*.—Quantity per flower: Typically five in a single whorl. Length: About 3 cm. Width: About 1 cm. Shape: Roughly deltoid. Apex: Tapered. Base: Truncate. Margin: Entire; ciliated and/or glandular. Texture, upper surface: Pubescent; leathery. Texture, lower surface: Ciliated and/or glandular; along the margins, pubescent; leathery. Color: When opening, upper surface: Close to 146B to 146D. When opening, lower surface: Close to 144A and 175B. Fully opened, upper surface: Close to 146C to 146D. Fully opened, lower surface: Close to 144A and N144D.

*Pedicels*.—Length: About 3.9 cm. Diameter: About 3 mm. Strength: Moderately strong. Aspect: About 36° from vertical. Texture: Glandular, spiny. Color: Close to 144A and 145A.

*Reproductive organs*.—Stamens: Quantity: About 133 per flower. Anther length: About 2.7 mm. Anther shape: Reniform. Anther color: Close to N163D. Filament color: Close to 153D. Pollen amount: Moderate to abundant. Pollen color: Close to 163A. Pistils: Quantity: About 105 per flower. Pistil length: About 1.1 cm. Stigma shape: Broadly reniform. Stigma color: Close to 160B. Style length: About 7.3 mm. Style color: Close to 150D. Receptacle height: About 1 cm. Receptacle diameter: About 8 mm. Receptacle shape: Cup-shaped. Receptacle texture: Smooth, glabrous. Receptacle color: Close to 144A. Seeds: Seed production has been observed with about six seeds forming per fruit.

Pathogen & pest tolerance/resistance: Plants of the new Rose have been observed to be tolerant to *Botrytis*. Plants of the new Rose have not been observed to be tolerant or resistant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R136' as illustrated and described.

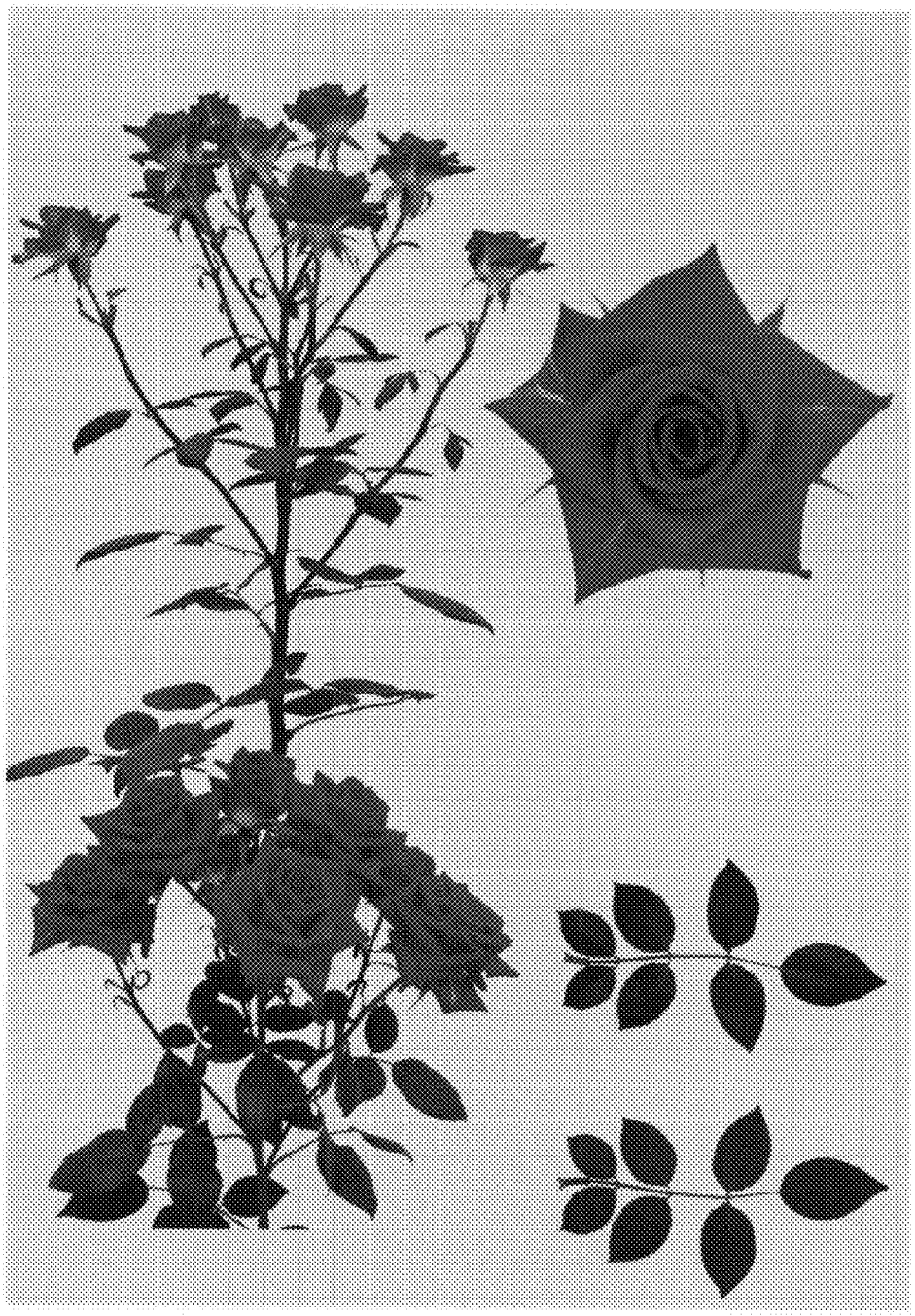

* * * * *